(12) United States Patent  
Lueckenhoff

(10) Patent No.: US 8,746,246 B2
(45) Date of Patent: Jun. 10, 2014

(54) APPARATUS AND METHOD FOR RETRIEVAL OF TUBING

(75) Inventor: Stephen A. Lueckenhoff, Albuquerque, NM (US)

(73) Assignee: Inspyrd Products Corporation, Albuquerque, NM (US)

( * ) Notice: Subject to any disclaimer, the term of this patent is extended or adjusted under 35 U.S.C. 154(b) by 321 days.

(21) Appl. No.: 12/794,635

(22) Filed: Jun. 4, 2010

(65) Prior Publication Data

US 2010/0307496 A1 Dec. 9, 2010

Related U.S. Application Data

(60) Provisional application No. 61/184,243, filed on Jun. 4, 2009.

(51) Int. Cl.
*B65H 75/48* (2006.01)
*B65H 75/44* (2006.01)

(52) U.S. Cl.
USPC .................... 128/204.18; 242/390.2; 242/388

(58) Field of Classification Search
USPC ............. 128/204.18, 205.22, 200.24, 202.27, 128/207.18; 242/390.2, 388, 378.4, 390.8, 242/169, 170, 227, 403; 137/355.12, 137/355.22
See application file for complete search history.

(56) References Cited

U.S. PATENT DOCUMENTS

| | | | |
|---|---|---|---|
| 3,625,450 A | 12/1971 | Lloyd | |
| 3,924,498 A * | 12/1975 | Hill | ................................. 83/58 |
| 4,187,962 A | 2/1980 | Henry | |
| 4,189,107 A | 2/1980 | Quenot et al. | |
| 4,624,141 A | 11/1986 | Soleau | |
| 4,685,634 A | 8/1987 | Schwartz | |
| 4,721,833 A | 1/1988 | Dubay | |
| 5,332,171 A | 7/1994 | Steff | |
| 5,392,808 A | 2/1995 | Pierce | |
| 5,444,919 A | 8/1995 | Alves | |
| 5,495,995 A | 3/1996 | Dominique et al. | |
| 5,558,118 A | 9/1996 | Mooring | |
| 5,647,554 A | 7/1997 | Ikegami et al. | |
| 5,826,608 A | 10/1998 | Pierce | |
| 5,947,148 A | 9/1999 | De Vito | |
| 5,975,120 A | 11/1999 | Novosel | |
| 6,065,490 A | 5/2000 | Falcone | |
| 6,382,241 B1 | 5/2002 | Setrum | |
| 6,416,009 B1 | 7/2002 | Iaciofano et al. | |
| RE37,824 E | 9/2002 | Pullen | |
| 6,474,588 B2 | 11/2002 | Valverde | |
| D472,133 S | 3/2003 | Ball | |
| 6,588,444 B2 | 7/2003 | Paplow et al. | |
| 6,591,858 B2 | 7/2003 | Peterson | |
| 7,104,491 B2 | 9/2006 | Vinding | |
| 7,350,736 B2 * | 4/2008 | Caamano et al. | ........... 242/390.9 |
| 2003/0084833 A1 | 5/2003 | Sheikholeslam et al. | |
| 2003/0213865 A1 | 11/2003 | Moon et al. | |
| 2005/0017117 A1 | 1/2005 | Moon et al. | |
| 2006/0186254 A1 | 8/2006 | Handley et al. | |
| 2006/0243282 A1 * | 11/2006 | Sackman et al. | ......... 128/205.22 |
| 2007/0175182 A1 * | 8/2007 | Stravitz et al. | .................. 53/576 |

* cited by examiner

*Primary Examiner* — Tan-Uyen T. Ho
*Assistant Examiner* — Mark Wardas
(74) *Attorney, Agent, or Firm* — Deborah A. Peacock; Justin R. Jackson; Peacock Myers, P.C.

(57) ABSTRACT

An apparatus and method for retrieval and dispensing tubing, particularly useful for oxygen tubing.

26 Claims, 20 Drawing Sheets

APPARATUS AND METHOD FOR RETRIEVAL OF TUBING

CROSS-REFERENCE TO RELATED APPLICATIONS

This application claims priority to and the benefit of the filing of U.S. Provisional Patent Application Ser. No. 61/184,243, entitled "Apparatus and Method for Remote Retrieval of Tubing", filed on Jun. 4, 2009, and the specification thereof is incorporated herein by reference.

BACKGROUND OF THE INVENTION

1. Field of the Invention (Technical Field)

Embodiments of the present invention relate to an apparatus and method for retrieval and storage of tubing, especially useful for oxygen-related tubing and the like.

2. Related Art

Users are often prescribed supplemental oxygen as a part of home therapy for lung or pulmonary disease or dysfunction, heart disease, low oxygen readings, post-surgery situations or cancer. Also, many users require supplemental oxygen for comfort. This supplemental oxygen is inhaled through the nose or mouth into the lungs and then diffuses into the blood stream and increases the amount of oxygen going to the cells. The majority of these users are required to use the oxygen 24 hours a day or possibly just during the night. Oxygen therapy can be delivered from large oxygen tanks, liquid oxygen tanks, or from an oxygen concentrator. The most common mode of oxygen delivery is from an oxygen concentrator.

An oxygen concentrator is an electrical device that converts 21% room oxygen into concentrated 95% oxygen that is delivered to the user (see FIG. 14). Users on continuous oxygen often utilize an oxygen humidifier (see FIG. 16) to provide humidity to the dry oxygen that is produced from the concentrator.

Durable medical equipment companies that provide home oxygen systems usually place the oxygen concentrator in the user's bedroom. Other locations where oxygen concentrators might be located are the living room, a family room or other central area of the home. If a user is in a particular room of the house where the concentrator is located and subsequently walks into another room the tubing hanging from the user's nose is dragged behind the user and lies on the floor. This tubing can be up to 100 feet in length, or more. When the user decides to return to the first room, the user has to walk over or around the lengthy feet of tubing that leads back to the concentrator. This process of walking over or around oxygen tubing lying on the floor is difficult and potentially dangerous, especially if a user is using a walker to assist his/her ambulation. Many users complain of getting their feet tangled up in the tubing.

Embodiments of the present invention comprise a method and apparatus for retrieving lengths of tubing, including remotely, thus eliminating the potential hazard of tubing obstructing or impeding movement. The present invention also comprises a method and apparatus for ensuring that too much tubing is not retrieved at once.

BRIEF SUMMARY OF THE INVENTION

Embodiments of the present invention comprise apparatuses for retrieval and storage of a length of tubing comprising a motor attached to a rotatable spool, the rotatable spool enclosed in a housing and providing spooling and dispensing of the tubing, a control system comprising a microprocessor; and the control system controllable manually or automatically to dispense and retrieve the tubing.

Embodiments of the present invention comprise methods for retrieving and storing of tubing comprising connecting a motor and a rotatable spool system, providing a length of tubing, spooling and dispensing the tubing on the rotatable spool system and controlling, manually and automatically, the spooling and retrieving of the tubing.

Further scope of applicability of the present invention will be set forth in part in the detailed description to follow, and in part will become apparent to those skilled in the art upon examination of the following, or can be learned by practice of the invention. The objects and advantages of the invention can be realized and attained by means of the instrumentalities and combinations particularly pointed out in the appended claims.

BRIEF DESCRIPTION OF THE SEVERAL VIEWS OF THE DRAWINGS

The accompanying drawings, FIGS. 1 through 24 in the attachment which are incorporated into and form a part of the specification, illustrate one or more embodiments of the present invention and, together with the description, serve to explain the principles of the invention. The drawings are only for the purpose of illustrating one or more preferred, embodiments of the invention and are not to be construed as limiting the invention. In the drawings.

DETAILED DESCRIPTION OF THE INVENTION

Embodiments of the present invention relate to an apparatus and method for retrieving lengths of tubing, including but not limited to oxygen supply tubing, by using a motorized spool which rotates to retrieve the tubing and thereby substantially prevents, minimizes or eliminates a tripping hazard.

Preferably, embodiments of the present invention are made of a rigid material, preferably plastic and/or fiberglass and the like. Alternative embodiments are collapsible and/or portable. The present invention is useful for and may further comprise crimp-free oxygen tubing and the like which has free and/or low resistance to pull out for retrieval. Embodiments of the present invention can be portable and/or stationary. Optionally, embodiments of the present invention are battery operated and/or can use any appropriate alternative power source. Alternatively, embodiments can be opened and/or enclosed in a cage, box, oxygen supply device and/or any combination thereof.

The term "fluid," as used throughout the specification, is defined to include, but is not limited to, a continuous amorphous matter that tends to flow and conform to the outline of its container, such as a liquid or a gas.

The term "tubing," as used throughout the specification, is defined to include, but is not limited to, conduit consisting of a long object, usually cylindrical, and usually hollow, used to hold and conduct objects or liquids or gases, and any other non-hollow materials including cord, rope and the like.

Figure 1:
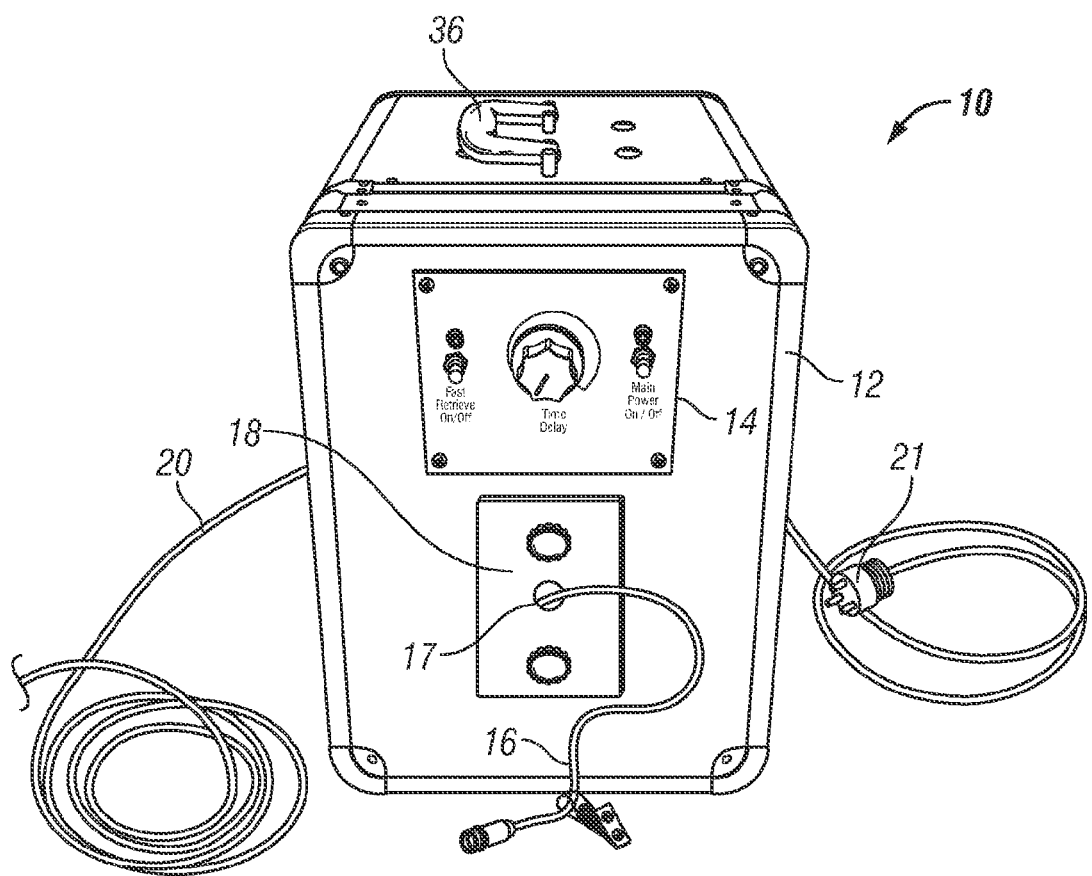
FIG. 1 illustrates an external view of an embodiment of the present invention.

As shown therein, FIG. 1 illustrates an embodiment of retrieval apparatus 10 comprising housing 12, control panel 14, user tubing 16, tubing changeout plate 18, inlet supply tubing 20 (usually from oxygen generating device) and electrical supply cord 21. Tubing changeout plate 18 comprises external tubing outlet hole with easy tubing change out knobs 76 (see FIG. 10). User tubing 16 is preferably dispensed and retrieved out of the tubing outlet hole 17 located on the front of retrieval apparatus 10. The motor, when in the off position, is free spinning, allowing the tubing to be easily unrolled off of the spool, as the user pulls the tubing our of the housing. The motor, when in the on position, has the ability to rotate clockwise or counterclockwise, thus retracting the tubing. The drawings illustrate some of the embodiments of the present invention.

These embodiments preferably provide easy and safe dispensing and retrieval while preventing the tangling of tubing.

Figure 2:
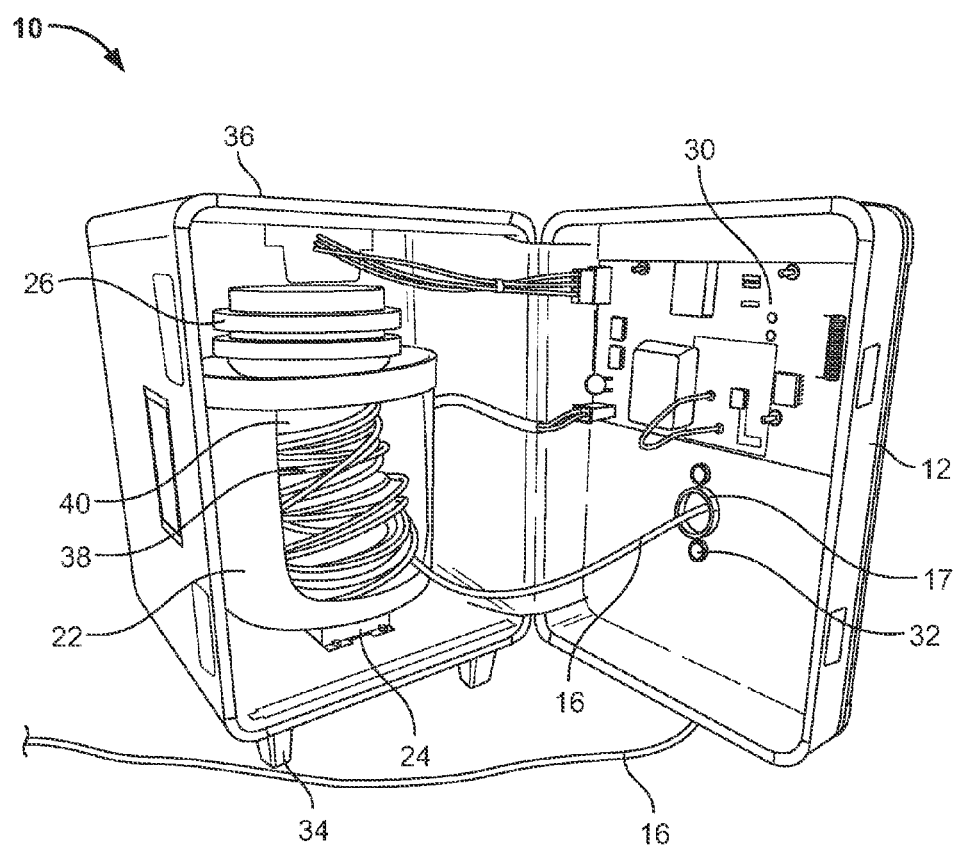
FIG. 2 illustrates an internal view of the FIG. 1 embodiment.

FIG. 2 illustrates an internal view of the FIG. 1 embodiment. Retrieval apparatus 10 includes but is not limited to housing 12, user tubing 16, tubing outlet hole 17, spool casing 22, spool support block 24, rotary motor 26, stabilizing motor bracket 28, microprocessor 30, mounting brackets 32, feet 34, handle 36, connector tube 38, and spool 40. Retrieval of tubing 16 is accomplished via rotary motor 26 that is directly attached to spool 40. The suspension of motor 26 and integrated spool 40 assembly results in easy manual dispensing of tubing with minimal resistance for the user, when the user pulls tubing 16 out of outlet hole 17. Because dispensing is manual, only the amount of tubing 16 that the user requires is dispensed. Computer memory in microprocessor 30 preferably retains the previous setting of retrieval apparatus, in the event of a power outage or power fluctuation. Microprocessor 30 also preferably retains user information, including but not limited to the user preferences (e.g. short pulls or retrievals versus longs pulls or retrievals, predetermined retrieval lengths, times of access, etc.). Alternative embodiments include automatic and/or mechanized dispensing of user tubing.

Motor 26 rotation and retrieval function is preferably controlled by closed circuit microprocessor 30 that is programmed to initiate activation of a plurality of modes including but not limited to pre-set time dependant retrieval cycles. Motor 26 preferably provides low torque. For example, if during the retrieval cycle, an increase in tubing 16 resistance is detected, motor 26 stops rotating, stopping the retrieval process, and prevents oxygen cannula 82 (see FIG. 15) from being pulled out of the nose of the user.

Figure 3:
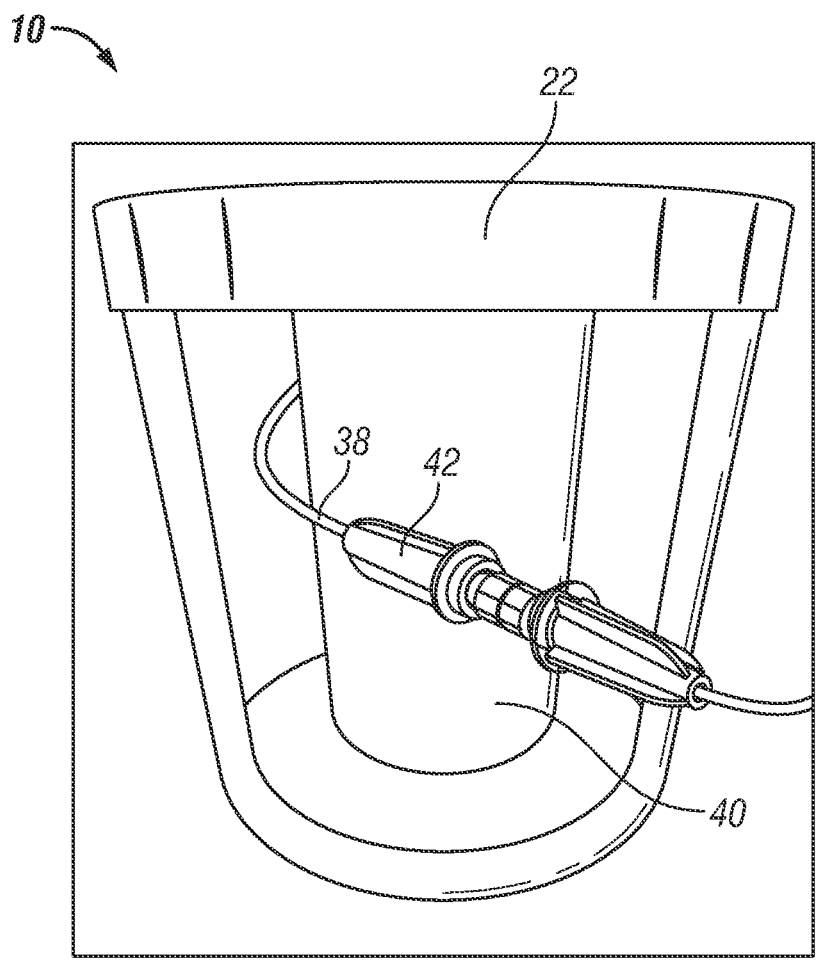
FIG. 3 illustrates an embodiment of a spool and connector tubing.

FIG. 3 illustrates an embodiment of the spool and connector tubing of the present invention. Embodiments include but are not limited to a casing enclosing the motorized portion of the invention. Embodiments of the present invention preferably comprise motor 26 (see FIG. 2), which can include but is not limited to a pancake motor. Retrieval apparatus 10 is illustrated comprising spool 40, connector tubing 38 and spool casing 22. Smaller torque reduces the possibility that an oxygen cannula tubing can be yanked and/or pulled off of a user's face. The motor of the present invention is preferably sparkless. Motor 26 (see FIG. 2) has sufficient torque to turn integrated spool 40, and optionally utilizes a direct drive and/or an indirect drive. Retrieval apparatus 10 preferably comprises tubing 16 exiting at top of spool 40 (see FIG. 4). Retrieval apparatus 10 preferably comprises a containment reservoir to prevent tubing 16 from dropping under spool 40. Retrieval apparatus 10 comprises connector tubing 38 preferably connected to swivel adapter 42 connected to user tubing 16 on one end and connected via another swivel adapter on the other end which then connects to the oxygen concentrator. Connector tubing 38 is optionally approximately 8 to 12 inches in length and aids in the prominent safety features of the invention including but not limited to preventing tubing disconnection. The connection system of connector tubing 38 to swivel adapter 42 to user tubing 16 preferably causes a reduction in diameter of tubing through outlet hole 17, thereby allowing only user tubing 16, and not swivel adapter 42 and tubing connector 46 (see FIG. 4) to pass through tubing outlet hole 17.

Figure 4:
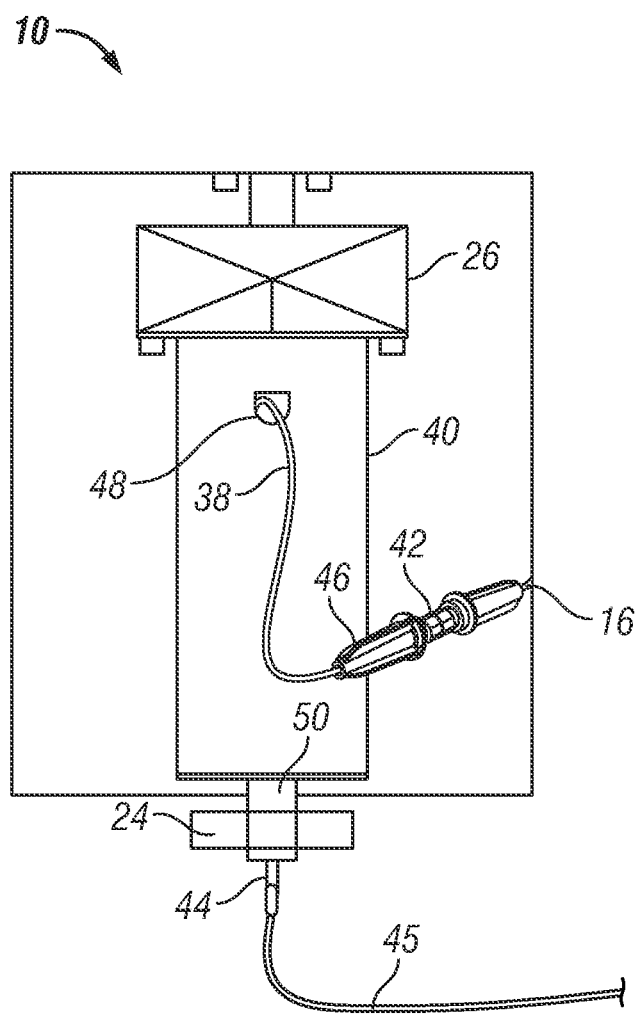
FIG. 4 illustrates an internal view of the FIG. 1 embodiment.

FIG. 4 is an illustration of an internal view of an embodiment of the present invention. Retrieval apparatus 10 includes but is not limited to tubing 16 for user, spool support block 24, rotary motor 26, connector tube 38, spool 40, swivel adapters 42 and 44, and oxygen inlet supply tube 45 to oxygen concentrator, connector tube outlet hole 48 and spool holder 50.

Embodiments of the present invention preferably include but are not limited to a spool that is large enough to accommodate many feet of tubing (e.g. up to 100 feet of oxygen tubing) and a motor that can be operated with a remote control device, optionally housed inside a wood, metal or plastic case or the like, or any combination thereof, optionally with legs and/or rollers to allow for lift of the apparatus off of the floor and are optionally made of or coated with a material that prevents sliding of the apparatus on the floor or carpet. Embodiments of the present invention comprise various or alternate spool sizes. The present invention comprises an embodiment that accommodates greater lengths of tubing upon adjusting electronic settings and using alternate spool sizes.

Figure 5:
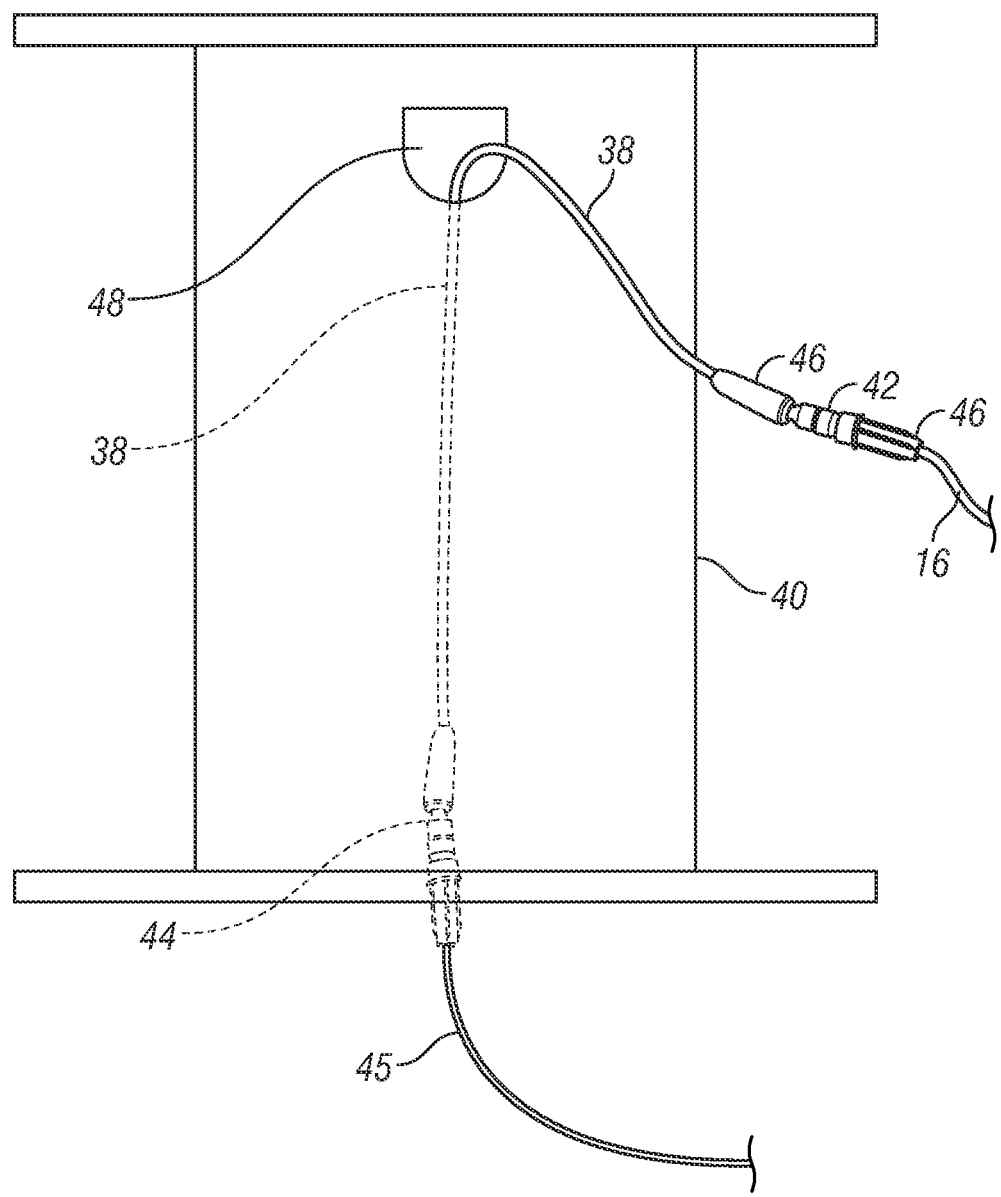
FIG. 5 illustrates an internal view of the spool and tubing.

FIG. 5 illustrates an embodiment of the spool and connector tubing. Motor 26 (FIG. 2) preferably rotates spool 40. In this embodiment of the invention, connector tube 38 preferably passes internally up through spool 40 and out spool outlet hole 48, attaches to swivel adapter 42 by connector 46 and attaches to user tubing 16. Underneath spool 40, connector tube 38 attaches to swivel adapter 44 and inlet tubing 45 (e.g. from an oxygen concentrator). Spool assembly is preferably made of a plastic and/or fiberglass material or any rigid material and/or combination thereof.

Spool 40 preferably retrieves or retracts tubing onto spool 40 each time the remote or manual control button is depressed. The apparatus is designed to operate in a plurality of modes, most generally a short retrieve and a fast retrieve mode.

Figure 6:
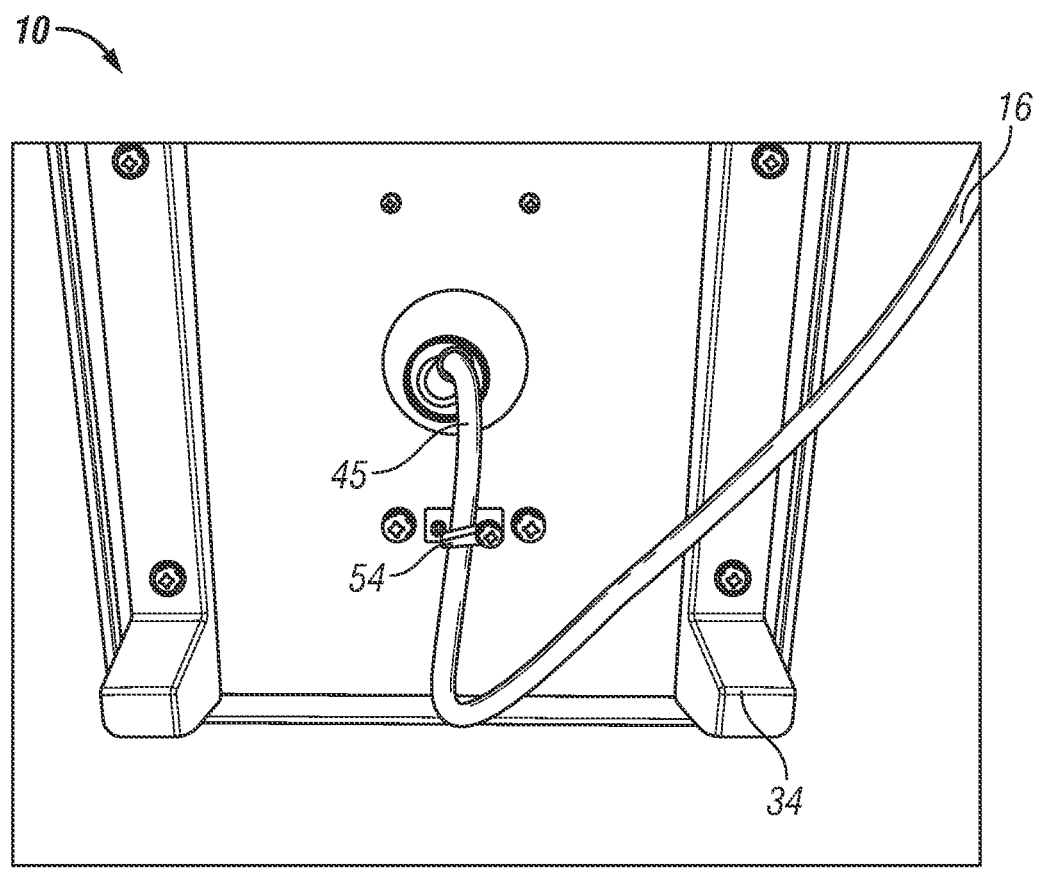
FIG. 6 illustrates the underside of the present invention with a tubing holder closed.
Figure 7:
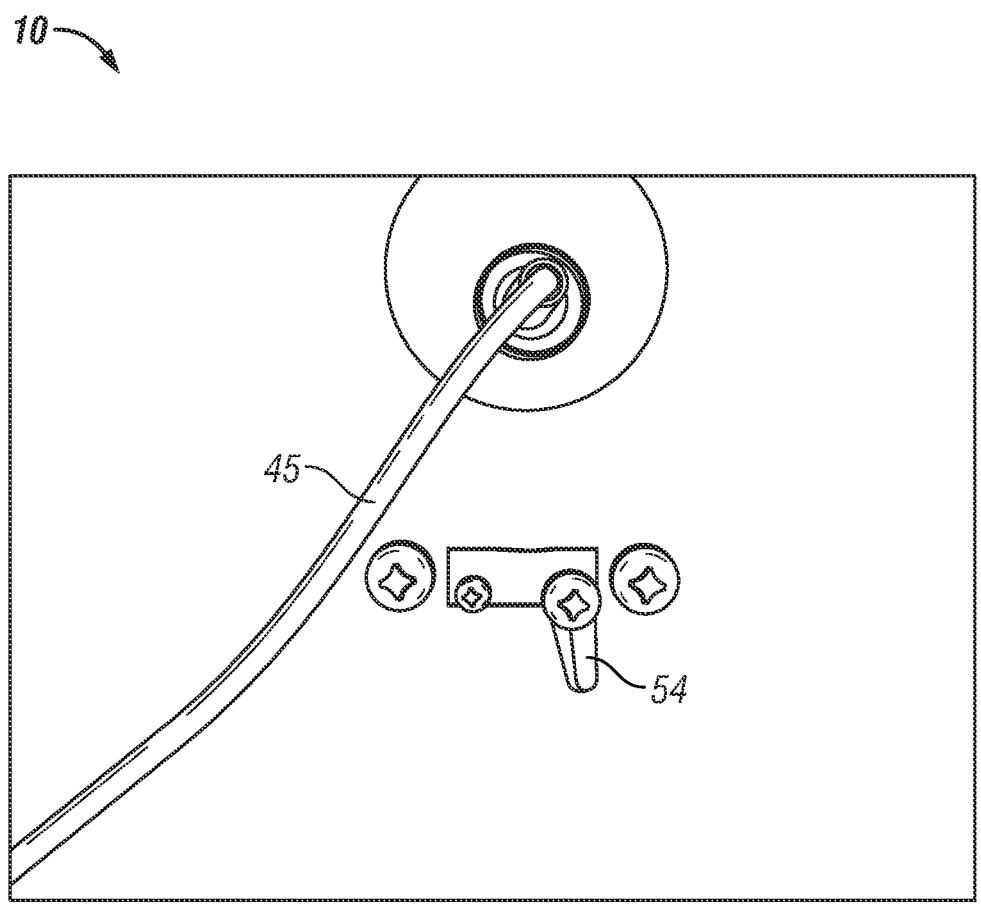
FIG. 7 illustrates the underside of the present invention with the tubing holder open.

In FIGS. 6 and 7, external inlet tubing 45 is illustrated as well as tubing holder or retainer 54. Tubing retainer 54 preferably secures, in a closed position (see FIG. 6), oxygen inlet tubing 45 that is generally attached to a source (e.g. an oxygen source). FIG. 7 illustrates tubing retainer 54 in the open position for ease of movement or replacement. Tubing retainer 54 optionally prevents inlet tubing 45 from accidental disconnection, swinging and/or getting caught on ancillary objects. Tubing retainer 54 preferably affixes the inlet tubing 45 to the bottom and/or underside of retrieval apparatus 10.

Figure 8:
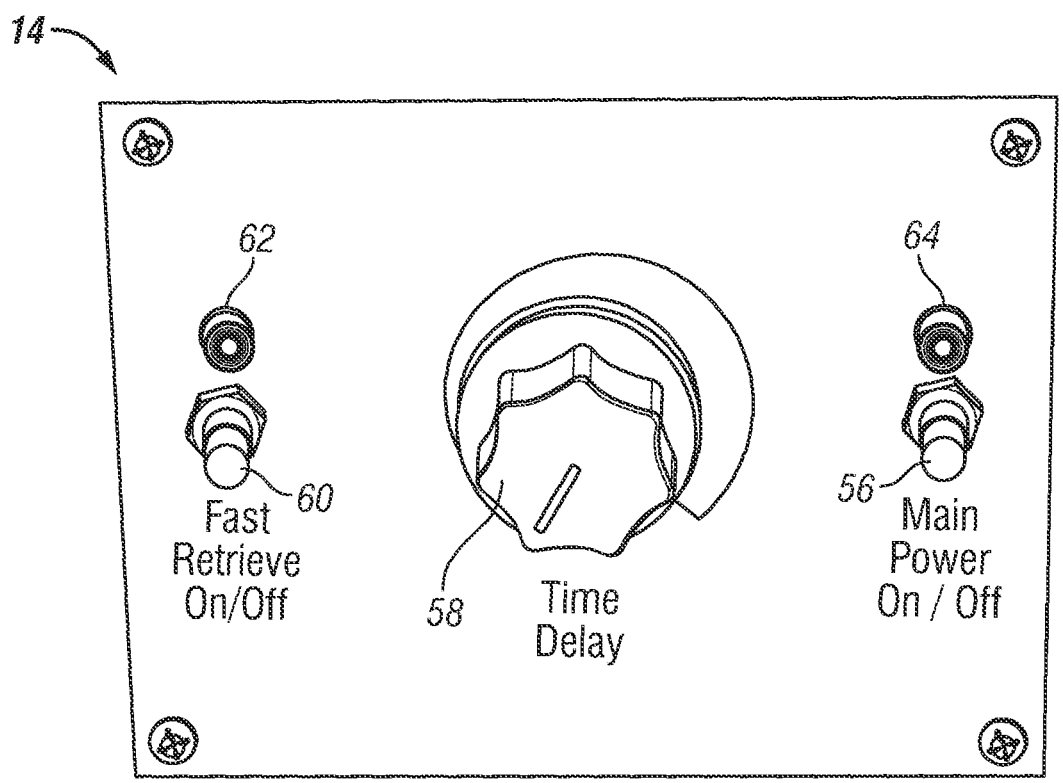
FIG. 8 illustrates an embodiment of a control panel.

An embodiment of control panel 14 is illustrated in FIG. 8. Controls are optionally internal and/or external to control panel 14 which can optionally be locked to ensure only authorized users set controls. Controls preferably include but are not limited to power switch 56, with associated power light 64. Delay and timing control 58 preferably comprise a plurality of delay settings. Time delay is especially important to allow a user to press the remote control button and then move to put that hand elsewhere, e.g. a walker. Optional retrieve (e.g. fast) on/off switch 60 and associated activation light 62 are located on an embodiment of control panel 14. Alternatively, settings can be changed and monitored if necessary. Control panel 14 comprises at least one potentiometer. Control panel 14 preferably communicates with motorized spool 40 through microprocessor 30 (see FIG. 2).

Figure 9:
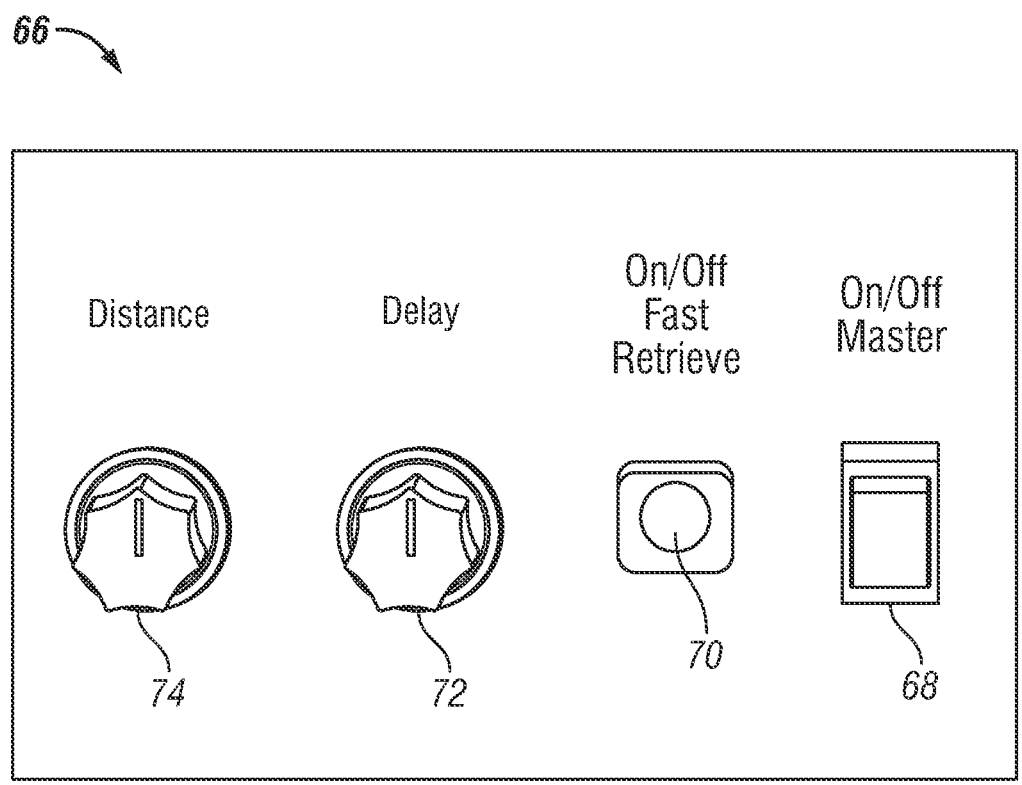
FIG. 9 illustrates an alternate embodiment of a control panel.

FIG. 9 illustrates an alternative embodiment of a control panel embodiment of the present invention. Control panel 66 optionally comprises on/off master switch 68, on/off retrieve (e.g. fast) toggle switch (optionally illuminated when on) 70, delay control knob 72, and/or optional distance control knob 74.

Figure 10:
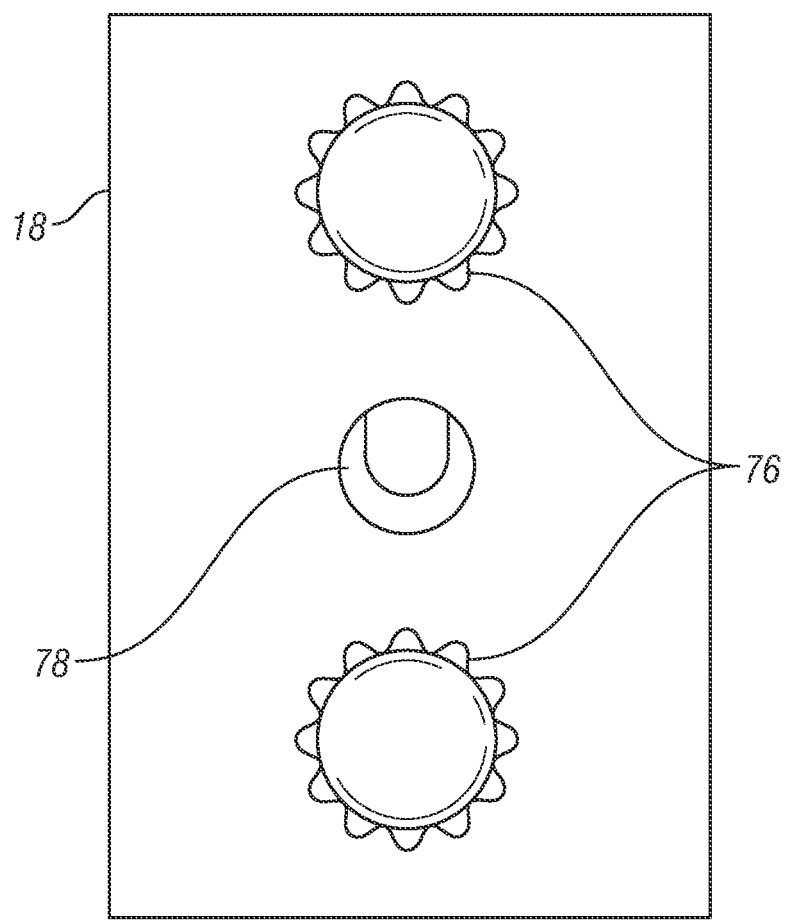
FIG. 10 illustrates a removable exterior tubing changeout plate.
Figure 11:
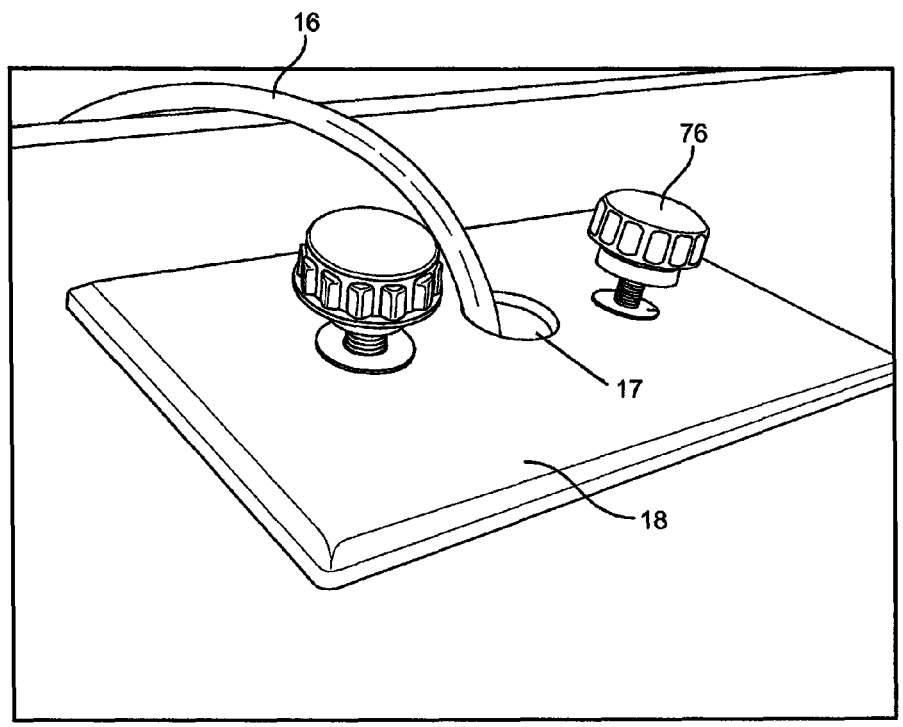
FIG. 11 illustrates a close view of the tubing changeout plate of FIG. 10.
Figure 12:
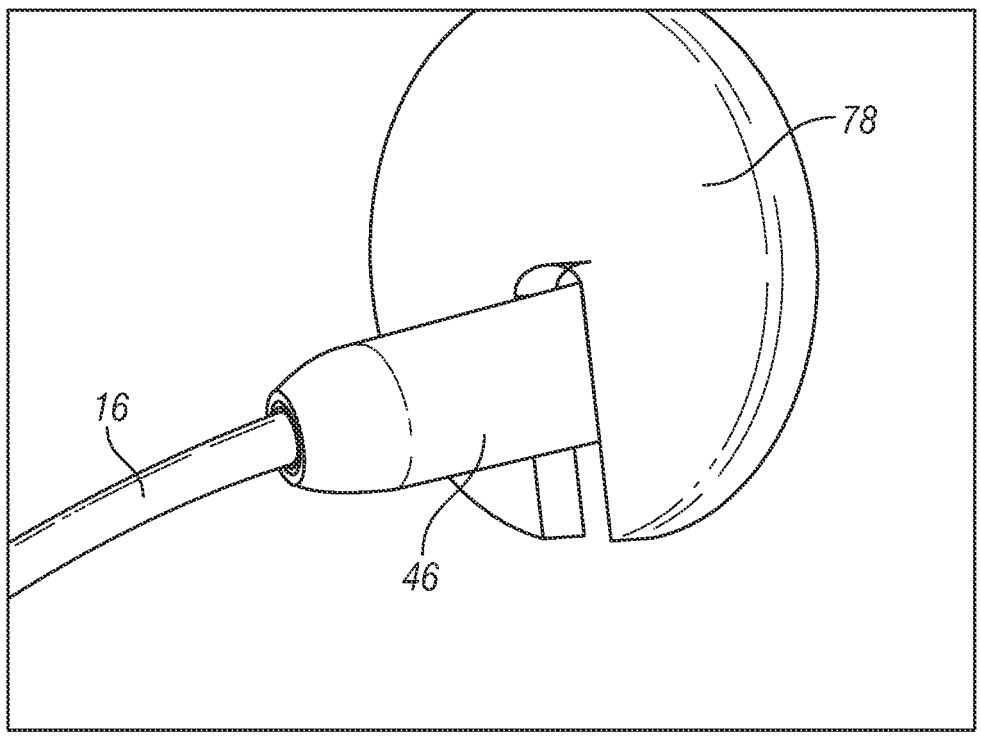
FIG. 12 illustrates an embodiment of a tubing disconnect preventer.

FIGS. 10 through 12 illustrate components of embodiments of the present invention to prevent accidental disconnection of user tubing 16 (see FIG. 11) from retrieval apparatus 10. Accidental disconnection of user tubing 16 could cause a loss of oxygen flow to the user. Prevention of accidental disconnection is accomplished in the present invention by use of adapters and connections through reduction in diameter of holes that prevent disconnection. FIG. 10 illustrates tube changeout plate 18 (see also FIG. 1), attachable to retrieval apparatus 10 with changeout knobs 76. Tube restrictor 78 further prevents disconnection from tubing because the swivel connector cannot pass therethrough. FIG. 11 illustrates an embodiment of the present invention comprising tube changeout plate 18 with changeout knobs 76 whereby user tubing 16 preferably flows out of tube outlet hole 17. FIG. 12 illustrates tube restrictor 78 restricting connector 46 from passing therethrough.

Figure 13:
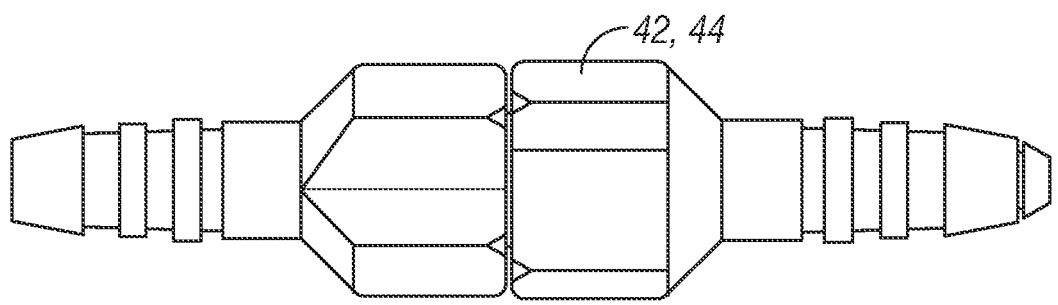
FIG. 13 illustrates a swivel adapter useful for the tubing.

FIG. 13 illustrates swivel adapter 42 and 44, which preferably allows for connection and ease of movement between sections of tubing and is useful in embodiments of the present invention. Swivel adapter 44 turns inside spool 40 to prevent tangling of the tubing attached to an external device. The bottom of swivel adapter 44 is connected to retrieval apparatus 10 to preferably rotate inlet supply tube 45. The top of swivel adapter 44 is preferably attached to connector tube 38 (see FIG. 2). Connector tube 38 preferably connects with swivel adapter 42 to user tubing 16, preferably allowing free rotation of user tubing 16 as spool 40 rotates. Other adapters for connecting numerous types of tubing may also be used in accordance with the present invention.

Figure 14:
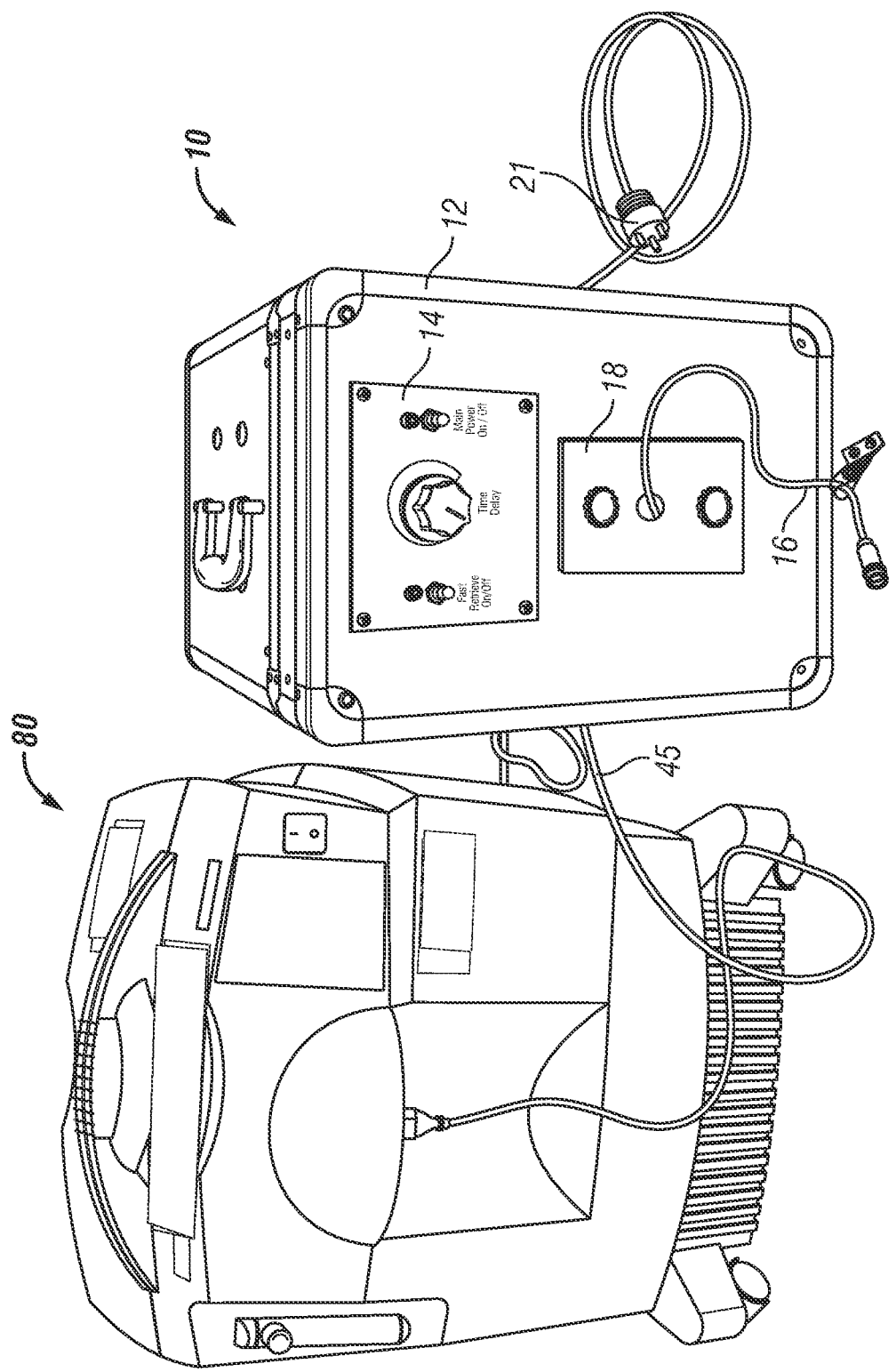
FIG. 14 illustrates an embodiment of the present invention attached to an oxygen concentrator.

FIG. 14 is a front view of an embodiment of the present invention 10 connected to an oxygen generating device, specifically oxygen concentrator 80. Retrieval apparatus 10 is connected by external tubing line 45 to oxygen concentrator 80. Retrieval apparatus 10 further comprises user tubing 16 and power cord 21. Retrieval apparatus 10 is preferably used in conjunction with a device that administers continuous oxygen to users, and these devices are readily known in the industry.

Figure 15:
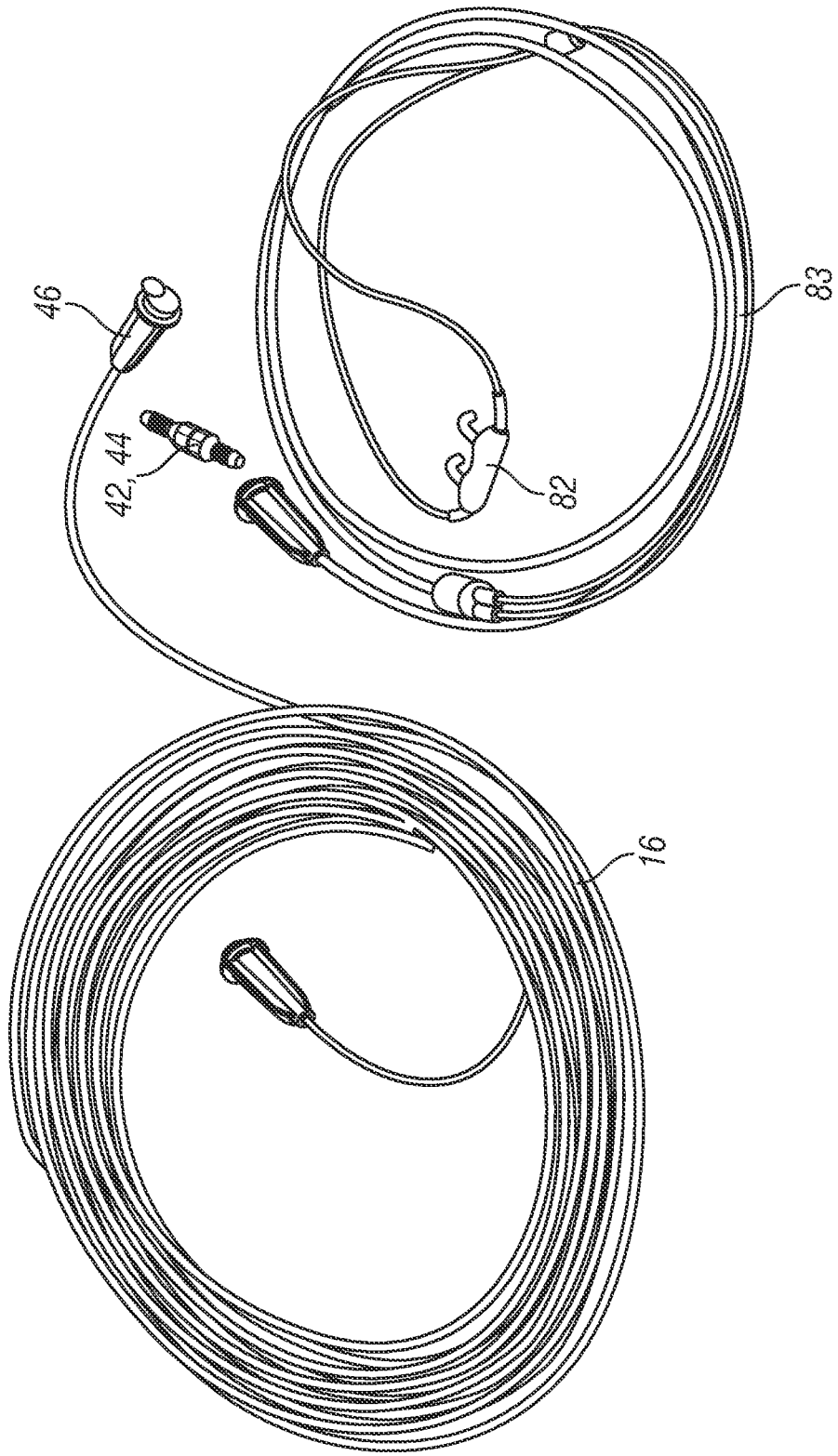
FIG. 15 illustrates oxygen tubing, a swivel adapter, and tubing attached to an oxygen cannula.

FIG. 15 illustrates user tubing 16 preferably including connector 46, oxygen cannula 82 and swivel adapter 42, 44. Oxygen is optionally administered through the use of oxygen cannula 82. Cannula 82 can be placed in a user's nose and is generally used for users requiring low to medium concentrations of supplemental oxygen. The majority of users receiving continuous oxygen therapy utilize an oxygen cannula 82, connected to cannula tubing 83, for the delivery of oxygen to the user's nose. Oxygen cannula 82 has tubing which is preferably approximately e.g. 7 feet in length and can be connected via standard connector 46 and swivel adapter 42, 44 to longer section of user tubing 16. Oxygen supply tubing manufactured for home use is generally 25 feet or 50 feet in length. When oxygen cannula 82 is attached to the user tubing 16, it preferably achieves a total length of tubing that is between approximately 32 feet long and approximately 57 feet in length but optionally is as much as 100 feet.

Figure 16:
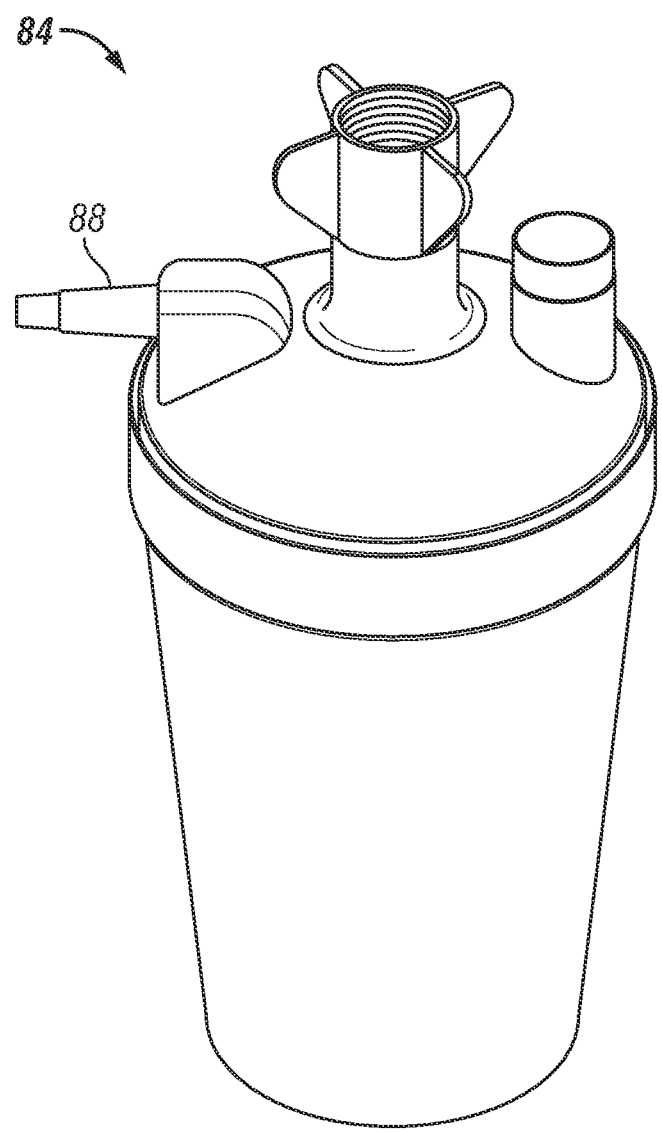
FIG. 16 illustrates an oxygen humidifier.

FIG. 16 illustrates an optional oxygen humidifier 84 that attaches to oxygen concentrator 80 as commonly used and well known in the art (see FIG. 14). Oxygen inlet tubing 45 has one end attached to oxygen humidifier 84 which is connected to oxygen concentrator 80. Oxygen inlet tubing 45 preferably connects to embodiments of the present invention through swivel adapter 42, 44, that connects to connector tube 38, then attaching to user tubing 16 preferably utilizing swivel adapter 42, 44. The other terminal end of user tubing 16 preferably attaches to tubing with cannula 82, and is inserted and worn in a user's nose.

Embodiments of the present invention optionally use remote control 90 (see FIGS. 17-24) to communicate with rotary motor 26 for retrieval of user tubing 16 (see FIG. 2). These embodiments optionally use remote control 90 to turn the motor on or off, when the user is located at the distal end of user tubing 16. User tubing 16 that can be retrieved is preferably between approximately 5 and approximately 100 feet, more preferably between approximately 25 and 75 and most preferably between approximately 40 and approximately 50 feet, in particular for oxygen tubing. Remote control 90 comprises safety features that prevent the accidental rapid retrieval of the user tubing 16. In order to provide the user free hands for use of a walker, cane and/or wheelchair and/or any assistive device, several options are currently available. Alternative embodiments include but are not limited to manual and/or semi-automated operation. Embodiments of the present invention include but are not limited to remote control 90 being worn on lanyard 92 that connects by lanyard connector 88 to connector portion 91 on remote control 90. Alternative embodiments include but are not limited to any chain and/or appropriate carrying mechanism for a remote control. When worn on a user with lanyard 92, remote control 90 preferably hangs approximately 10-15 inches long, measured from the bottom of a user's neck. Remote control 90 optionally has multiple addresses, up to at least millions, and can be capable of being manually changed if necessary, particularly if multiple retriever units are used in an area such as a nursing home.

The term "remote control" as defined throughout the specification includes but is not limited to any device that can be used to control a machine or apparatus from a distance.

Figure 17:
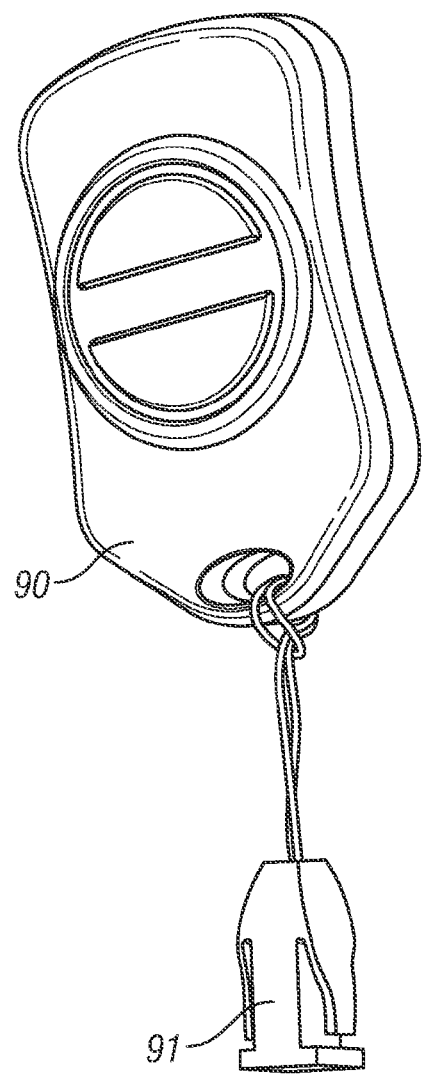
FIG. 17 illustrates an embodiment of a remote control.
Figure 17:
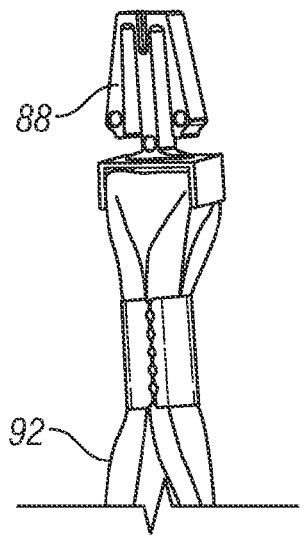
Figure 18:
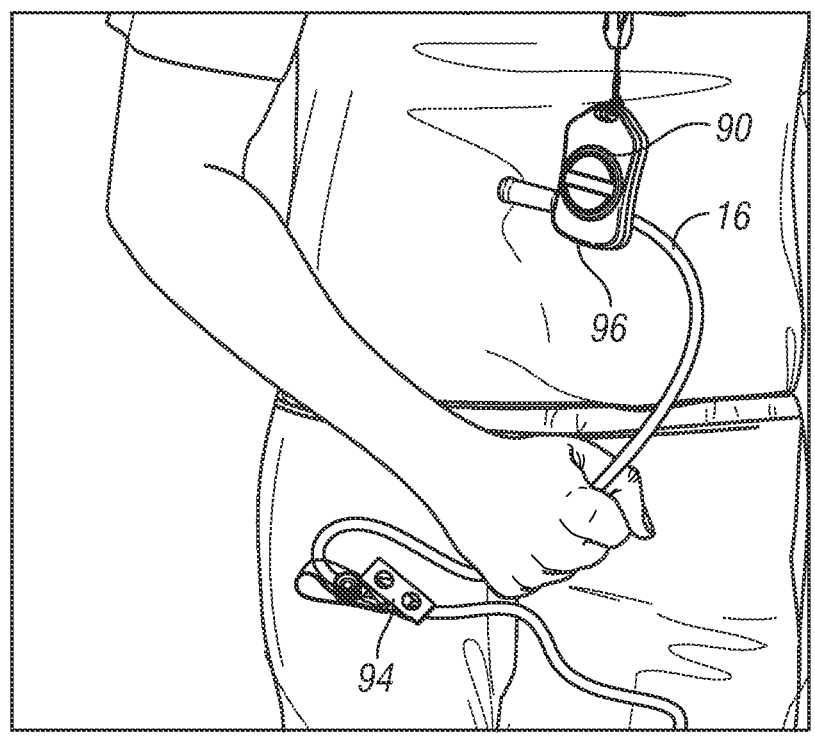
FIG. 18 illustrates embodiments of a safety clip, a remote control and a safety connection to a remote control.
Figure 19:
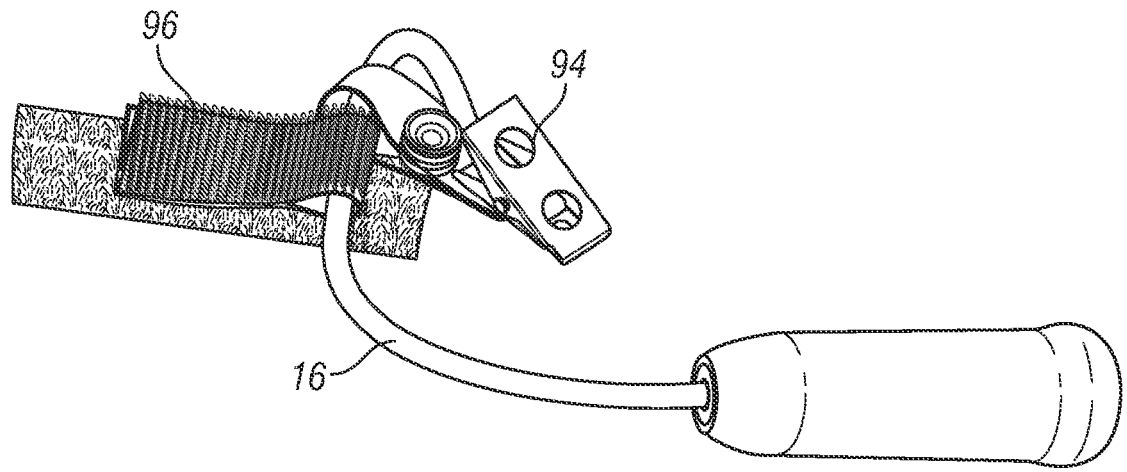
FIG. 19 illustrates tubing with an anchor and a spring loaded clip.
Figure 20:
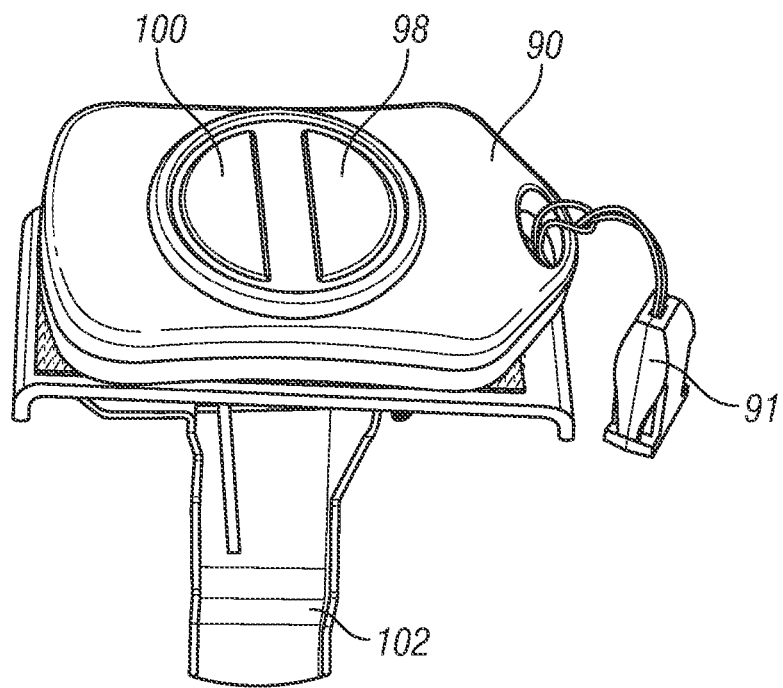
FIGS. 20-23 illustrate embodiments of a remote control attached to an anchor.
Figure 21:
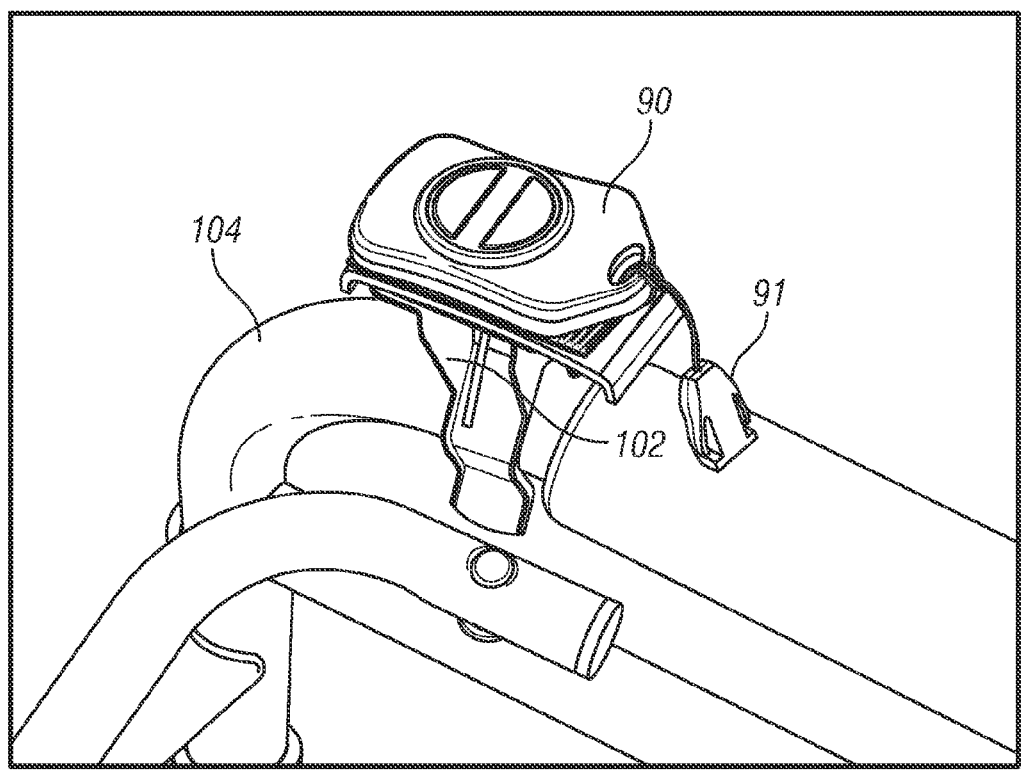
Figure 22:
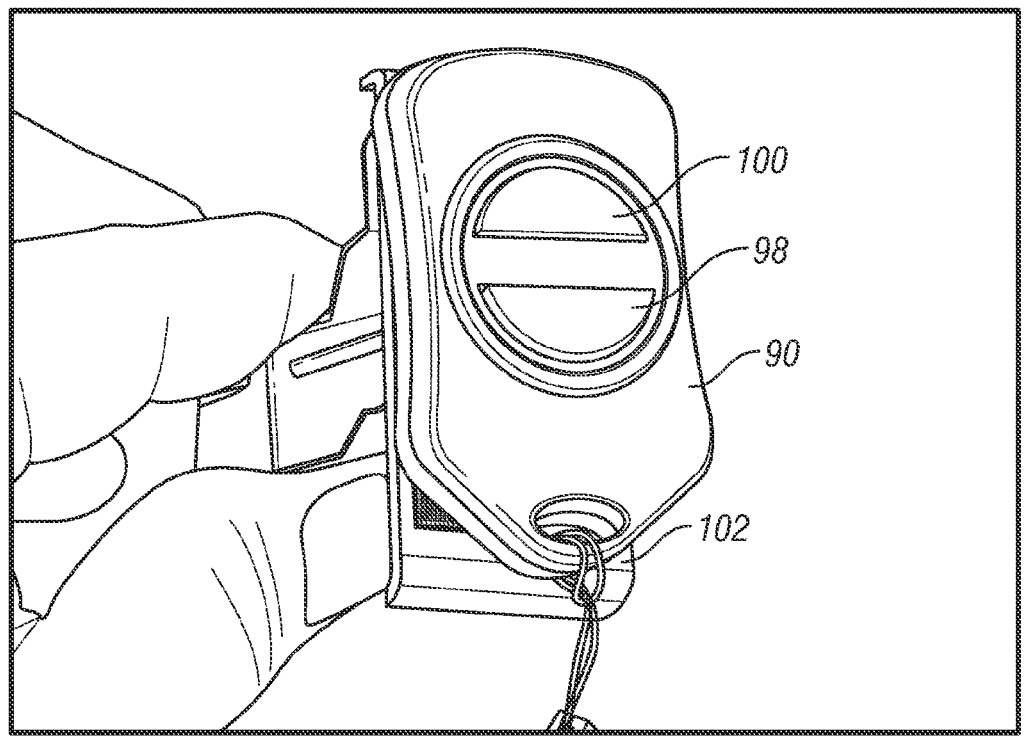
Figure 23:
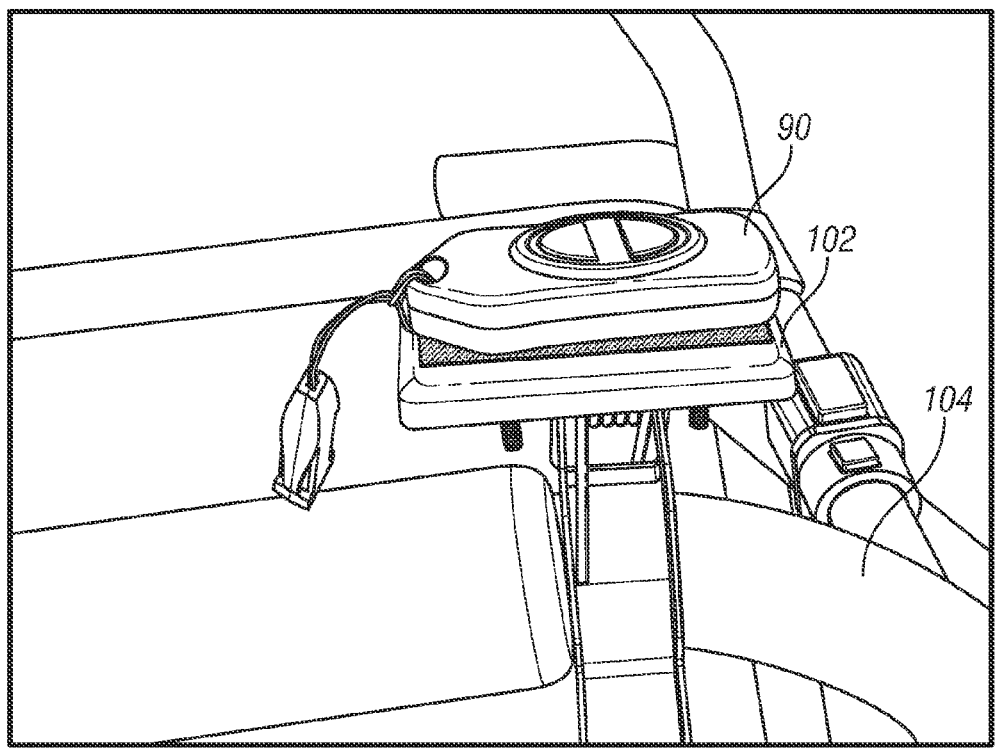
Figure 24:
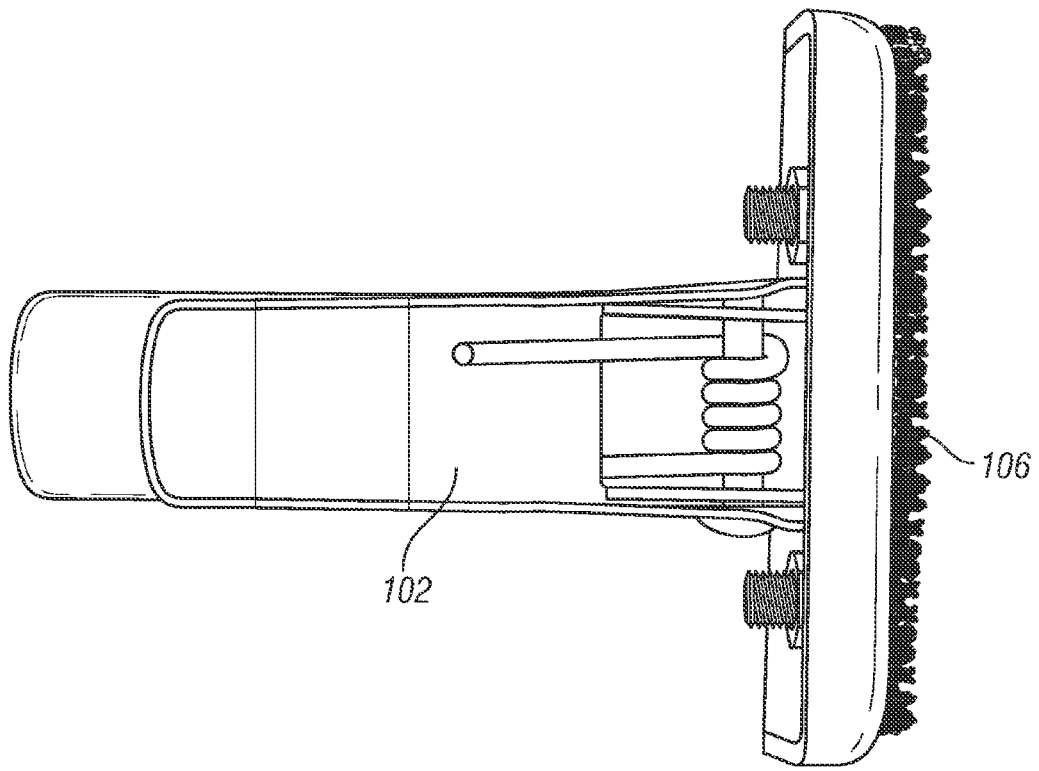
FIG. 24 illustrates an anchor embodiment of the present invention.

Illustrated in FIG. 18 is an embodiment of remote control 90, hanging on user's neck with lanyard 92 (FIG. 17). Additionally, spring loaded clip 94 is preferably affixed to user tubing 16, providing the capability for the user to attach the clip to clothing as an additional relief to pulling torque/tension being transferred or pulling on user's oxygen cannula on the face. User tubing 16 is preferably attached to remote control 90 to preferably assist in preventing movement against cannula 82 (see FIG. 15) on user's face. FIG. 19 illustrates spring loaded clip 94, and attachment strip 96 to preferably attach user tubing 16 to remote control 90.

Control panel 14 (FIG. 1) and microprocessor 30 (FIG. 2) work in combination to communicate and respond to commands from the user. FIGS. 20-23 illustrate remote control 90 with short retrieve button 98 and long retrieval button 100. Each depression of short retrieve button 98 can retrieve approximately tubing at a predetermined and preset length (for oxygen tubing preferably 15 to approximately 20 inches of user tubing 16, in approximately two seconds at zero time delay). This allows the user to walk smoothly and without impediment. Each depression of long retrieve mode button 100 can retrieve tubing at a longer length that is predetermined and preset (for oxygen tubing, preferably between approximately 48 to 60 inches of user tubing 16 in approximately four seconds). Time delay control 58 (FIG. 8) controls both short retrieve and long retrieval modes. Time delay control 58 comprises a rheostat and is preferably located externally on the housing of the motor/spool, which optionally allows the user to set delays of 0 seconds to 8 seconds of delay time after any remote control button is depressed, before retrieval of the tubing is initiated. This delayed period preferably allows the user who is using a walker and/or wheel chair, and/or other assistive device enough time after depressing the remote control button for them to grasp the walker before moving forward. Optionally the slack of the tubing is pulled from the front rather than pulled from the back.

Embodiments of the present invention include a plurality of safety features including but not limited to preferably preventing accidental retrieval of all of the tubing in the event that the button is continually depressed. The delay response feature gives the user time to grasp walker/wheel chair and/or other assistive device after the remote control button has been depressed. Remote control 90 preferably has an adjustable retrieval speed control mounted on the unit to customize tubing retrieval, based on the user's walking pattern.

In an alternative embodiment, short retrieve button 98, is optionally designated by a color on remote control 90. Fast retrieve mode button 100 is optionally designated by a different color in this embodiment. Each button preferably comprises a safety feature associated with depression of the button. When a button is depressed, it initiates retrieval, either immediate or delayed. Optionally, buttons can be designed to have a depress/release mode. When a button is depressed and not released, only the initial retrieval response can be accepted by the retrieval mechanism. The motor of the retrieval mechanism preferably does not continue to retrieve tubing if a button is accidentally depressed and not released. Another retrieval cycle can alternatively be initiated only when the button is released and subsequently depressed.

Embodiments of the present invention further comprise a time delay retrieval function that provides significant safety for the user, particularly for the user with slow reaction time, or the user ambulating in a walker or wheel chair. These users typically, due to the necessity to use his/her hands to support themselves during ambulation, require time after activating a retrieval button, to resume their hand position on a walker or wheelchair. The delay time function provides ample time for the user to return their hands to the ambulation device. Users with slow reaction time or that walk slowly can also benefit from the use of the time delayed retrieval.

Control of user tubing 16 retrieval is optionally a combination of microprocessor 30 and fast retrieve on/off switch 60 and remote control 90. This embodiment provides a safety feature to the user by preventing long retrieval for the user who ambulates slowly or for the confused user, who should only have the ability to retrieve the oxygen tubing in short lengths using short retrieve button 98. This embodiment is preferably activated on control panel 14, by depressing and holding fast retrieve button 60 until the illuminated light 62 goes off. When this mode is activated, it prevents long retrievals from being initiated when the long retrieval button 100 is inadvertently depressed on remote control 90.

Alternatively, any speed and/or safety combination can be used with the present invention. Delay time can optionally be increased.

Embodiments of the present invention can also include but are not limited to mounting the remote control by the use of hook and loop or similar material connecting devices onto a walker and/or a wheel chair and/or any assistive device and the user depressing the remote control button at convenient intervals. These embodiments are illustrated in FIGS. 20-24. Alternatively, embodiments of the present invention can be manually controlled.

Embodiments of the present invention can also comprise remote control walker/wheelchair/assistive device mounting bracket 102. An embodiment of mounting bracket 102 is illustrated with remote control 90. Mounting bracket 102 preferably connects to a horizontal bar of a walker and/or wheel chair 104 and/or any device (see FIGS. 21 and 23). Mounting bracket 102 is optionally made of a plastic plate and/or similar material and comprises, at least one grip portion and optionally provides platform 106 (FIG. 24) for connection of remote control 90. A hook and loop adhesive strip or other connective material is preferably affixed to the plastic plate. Remote control 90 optionally includes a female hook and loop adhesive strip attached to the bottom of remote control 90. Alternatively, any appropriate mounting mechanism can be used with remote control 90.

Embodiments of mounting bracket 102 preferably comprise a spring clip comprising a plastic plate or other material (e.g. 1-1.5 inches wide by two inches long), which is preferably connected to the top of the clip. A male hooked hook and loop adhesive strip is affixed to the plastic plate and the like. Alternative embodiments can be any size or shape as necessary to fit clothing or an assistive device.

Alternative embodiments of the present invention can include but are not limited to a voice-activated remote control, infrared, wireless, and/or any transmitting capability to initiate the retrieval of tubing. Alternative embodiments may comprise use of a password and/or a battery.

Alternative embodiments of the present invention can include but are not limited to retrieving any type of tubing, including but not limited to rope retrieval, wire retrieval, garden hose retrieval, high-pressure hose retrieval, and electrical extension cord retrieval. Other embodiments include use of the retrieval apparatus with box, canister, portable or other associated devices. Alternative embodiments can utilize any adequate power source. Alternative embodiments can use any engine and/or power source.

Other alternative embodiments include manual systems, and systems that can be used for underwater, hazardous environment and/or subterranean uses.

Alternative embodiments of the present invention can include but are not limited to battery-operated retrieval apparatuses.

Embodiments of the present invention include but are not limited to the remote control being carried in the user's hand and the user depressing the remote control button after each step walked.

Features of embodiments of the present invention include but are not limited to:

Lightweight, portable, equipped with handle.

Automated retrieval of tubing.

Electrically or battery powered unit.

Accommodates many feet (e.g. up to 100 feet) of tubing.

Provides multiple modes of retrieval.

Short retrieve mode—retrieves a predetermined shorter length of tubing.

Long retrieve mode—retrieves a predetermined longer length of tubing.

Delayed mode—adjustable delay prior to initiating retrieval.

Adjustable settings, through the use of a microprocessor, so that retrieval lengths can be increased or decreased.

No gear design provides free spinning spool, resulting in minimal resistance when the user extracts tubing from the housing.

Safety features.

Motor design and using time limited activation, produces low torque transferal on tubing and user, resulting reduced possibility of accidental removal of oxygen cannula from the user's nose.

Fast retrieve on/off provides option to deactivate fast retrieve function on remote control.

Remote control is programmable to prevent multiple activations if button is continuously depressed. Only one activation of the depressed button's function occurs until the button is released and depressed a second time.

Accidental control switch activation/deactivation is prevented by programming that requires a timed (e.g. five second) depression of the button, prior to activation or deactivation of the function.

Computer memory in the microprocessor retains the previous setting in the event of a power outage.

Remote control optionally has multiple addresses, e.g. millions.

Remote control can be manually reprogrammed by the user for a new address.

If the remote control is damaged, the user can mechanically perform tubing retrieval by systematically depressing buttons on the control panel.

Disconnect prevention, through use of two-piece unit and offset alignment of tubing outlet hole, prevents the accidental disconnection of tubing inside the retrieval apparatus.

Tubing retainer prevents inlet tubing from being disconnected from unit.

Easy tubing change out provides the ability to remove old tubing from unit and enables replacement of all tubing.

Locking case provides safety to the user and the public from accidental contact with electrical components.

Utilizes crimp resistant tubing, thereby preventing the reduction of stoppage of flow or tubing to the user.

Utilizes swivel adapters to prevent coiling or twisting of tubing after it has been dispensed from the spool.

Skid proof legs and leg placement prevent unit from sliding on the floor and also prevents unit from tipping over.

Large grounded electrical plug provides easy use for seniors or individuals with arthritis.

Large delay dial provides easy use for seniors or individuals with arthritis.

Mounting bracket for remote control enables the user easy use of remote control on a wheel chair or a walker.

Spring loaded clip attached to tubing and clipped onto the user's clothing provides additional relief to pulling torque/tension from being transferred or pulling on the user's cannula on the face.

Microprocessor memory provides capability to obtain information regarding the number of activations of the short and long retrieval functions.

INDUSTRIAL APPLICABILITY

Example 1

The present invention was operated as follows. An electric cord was connected from the motor to the remote control receiver, which was then plugged into an AC 125 volt electrical outlet (standard U.S. home electrical outlet). The user walked 50 feet away from the motor and spool device, holding the distal end of the oxygen tubing. The delay control knob on the control panel (see FIG. 8) was rotated to initiate a 0 second delay time after "short retrieve" button was depressed. The user depressed the short retrieve button on the remote control switch. The remote control operated on a DC 12 volt alkaline Battery (size A23). The oxygen tubing, approximately 18 inches, was immediately retrieved. When the OFF button was depressed, the motor stopped immediately, stopping the retrieval of the oxygen tubing. The remote control had a radio frequency of 315 MHZ with a range up to 50 feet.

Fifty (50) feet of oxygen tubing was used by a user, either by connecting two 25-foot lengths of tubing or using a single 50-foot length of tubing. The 25-foot length of oxygen tubing was replaced with a single 50-foot length of oxygen tubing. The motor had sufficient torque to retrieve the 50 feet of tubing.

Example 2

The present invention was operated as follows. An electric cord was connected from the motor to the remote control receiver, which was plugged into an AC 125 volt electrical outlet (standard U.S. home electrical outlet). The "DELAY" control knob, on the control panel was rotated to initiate a 2 second delay time after the "SHORT RETRIEVE" button was depressed. The user depressed the "SHORT RETRIEVE" button on the remote control switch. The oxygen tubing, approximately 18 inches, was retrieved after the 2 second delay time. The motor stopped immediately, stopping the retrieval of additional oxygen tubing.

Example 3

The present invention was operated as follows. An electric cord was connected from the motor to the remote control receiver, which was plugged into an AC 125 volt electrical outlet (standard U.S. home electrical outlet). The "DELAY" control knob, on the control panel was rotated to initiate a 2 second delay time after the "LONG FAST RETRIEVE" button was depressed. The "LONG FAST RETRIEVE" on/off switch or the control panel was depressed to the ON position.

The user depressed the "LONG FAST RETRIEVE" button on the remote control switch. The oxygen tubing, approximately 50 inches was retrieved after the 2 second delay time. The motor stopped immediately, stopping the retrieval of additional oxygen tubing Example 4

The present invention was operated as follows. An electric cord was connected from the motor to the remote control receiver, which was plugged into an AC 125 volt electrical outlet (standard U.S. home electrical outlet). The "DELAY" control knob, on the control panel was rotated to initiate a 0 second delay time after the "LONG FAST RETRIEVE" button was depressed. The "LONG FAST RETRIEVE" on/off switch on the control panel was depressed to the ON position. The user depressed the "LONG FAST RETRIEVE" button on the remote control switch. The oxygen tubing, approximately 50 inches, was retrieved immediately. The motor stopped immediately, stopping the retrieval of additional oxygen tubing.

Example 5

The present invention operated used as follows. An electric cord was connected from the motor to the remote control receiver, which was plugged into an AC 125 volt electrical outlet (standard U.S home electrical outlet). The "DELAY" control knob, on the control panel was rotated to 2 second delay time after the "LONG FAST RETRIEVE" button was depressed. The "LONG FAST RETRIEVE ON/OFF" switch on the control panel was depressed to the OFF position. The user depressed the "LONG FAST RETRIEVE" button on the remote control. The motor was not activated; no tubing was retrieved. The user then depressed the "SHORT RETRIEVE" button on the remote control. The oxygen tubing, approximately 18 inches, was retrieved after the 2 second delay. The motor stopped immediately, stopping the retrieval of additional tubing.

Example 6

The present invention was operated as follows. An electric cord was connected from the motor to the remote control receiver, which was plugged into an AC 125 volt electrical outlet (standard U.S home electrical outlet). The entire 50 feet of oxygen tubing was withdrawn out the front of the unit through the oxygen tubing outlet. The entire unit was then lifted three feet off the ground, with the suspension being performed only with the connection of the 50 foot tubing to the internal swivel connector and short internal tubing. No disconnection of tubing occurred. The long retrieve button was depressed, 5 times to successfully retrieve the 50 feet of tubing.

Example 7

Instructions for the operation of the present invention were provided as follows:
Normal Operation.
1. Plug system into wall outlet (120VAC, 60 Hz).
2. Press the MAIN POWER ON/OFF button to turn ON the system. The green light illuminates.
3. On the remote control, press the SLOW button and the unit reels in about one foot of tubing.

Fast Retrieve Option
1. With the unit turned ON, press and hold the FAST RETRIEVE ON/OFF button for five seconds to turn ON the FAST RETRIEVE mode. The yellow light illuminates.
2. Release the FAST RETRIEVE ON/OFF button.
3. On the remote control, press the FAST button and the unit reels in about five feet of tubing.
4. This mode can be disabled by pressing and holding the FAST RETRIEVE ON/OFF button for five seconds to turn OFF the FAST RETRIEVE mode. The yellow light turns OFF
Delay Retrieval
1. Rotate DELAY knob clockwise to provide a 0 to maximum of 8 seconds.
2. This delay occurs on both SHORT and LONG retrievals.
3. To remove DELAY, rotate knob counter clockwise to 0 setting.
Manual Retrieve Option (for Lost Remote Controls)
1. With the unit turned ON, press and hold the FAST RETRIEVE ON/OFF button.
2. Now, press and hold the MAIN POWER ON/OFF button.
3. Hold both buttons for five seconds. The unit retrieves about one foot of tubing.
4. Release both buttons.

The preceding examples can be repeated with similar success by substituting the operating conditions of this invention for those used in the preceding examples. Although the invention has been described in detail with particular reference to these preferred embodiments, other embodiments can achieve the same results. Variations and modifications of the present invention are obvious to those skilled in the art and it is intended to cover all such modifications and equivalents.

What is claimed is:

1. An apparatus for retrieval and storage of an oxygen tube comprising:
    a motor attached to a rotatable spool, said rotatable spool enclosed in a housing;
    a control system comprising a microprocessor, wherein said control system controls retrieving of the oxygen tube onto the rotatable spool or dispensing of the oxygen tube from the rotatable spool;
    retrieval buttons, said retrieval buttons comprising at least two buttons, one to initiate a long retrieval time period over which a first length of the oxygen tube is retrieved onto the rotatable spool and one to initiate a short retrieval time period over which a second length of oxygen tube is retrieved onto the rotatable spool;
    a safety feature whereby upon initiation of the button for a long retrieval time period, the short retrieval time period button is deactivated, and whereby upon initiation of the button for a short time period, the button for a long retrieval time period is deactivated; and
    an adjustable retrieval delay input device that delays activation of the retrieval time periods when any of the retrieval buttons are selected.

2. The apparatus of claim 1 wherein said apparatus exerts a torque on oxygen cannula which is less than an amount required to pull the oxygen cannula off of a user.

3. The apparatus of claim 1 further comprising a connection for connecting the oxygen tube to an oxygen cannula.

4. The apparatus of claim 3 wherein said oxygen tube is connected to user tubing, and said user tubing is connected to the oxygen cannula.

5. The apparatus of claim 1 wherein said apparatus is connected to an oxygen source.

6. The apparatus of claim 1 wherein said motor comprises low resistance or free spinning rotation.

7. The apparatus of claim 1 wherein said microprocessor comprises communication with a wireless device.

8. The apparatus of claim 7 wherein said wireless device comprises said retrieval buttons allowing a user to select at least two tubing retrieval speeds.

9. The apparatus of claim 8 wherein said safety feature prevents multiple activations if one of said retrieval buttons is pressed and not released.

10. The apparatus of claim 1 further comprising an assembly at an opening of said housing to prevent disconnection from said oxygen tube.

11. The apparatus of claim 1 further comprising tubing connectors.

12. The apparatus of claim 1 further comprising a clothing attachment fastener to prevent pulling of an oxygen cannula off of a user.

13. The apparatus of claim 7 further comprising a mounting device for attachment of said wireless device to a mobile assistive device.

14. The apparatus of claim 1 further comprising a multiple-mode retrieval input device.

15. The apparatus of claim 12 further comprising a tubing connector attached to said clothing attachment fastener.

16. An apparatus for retrieval and storage of an oxygen tube comprising:
a motor attached to a rotatable spool, said rotatable spool enclosed in a housing and orientated to rotate about an axis which is substantially vertical when said apparatus is positioned in its intended operating position;
a control system comprising a microprocessor, wherein said control system controls retrieving of the oxygen tube onto the rotatable spool or dispensing of the oxygen tube from the rotatable spool;
a wireless device comprising retrieval buttons, said retrieval buttons comprising at least two buttons, one button to initiate a long retrieval time period over which a first length of the oxygen tube is retrieved onto the rotatable spool and one button to initiate a short retrieval time period over which a second length of oxygen tube is retrieved onto the rotatable spool;
a safety feature whereby upon initiation of the button for the long retrieval time period, the short retrieval time period button is deactivated, and whereby upon initiation of the button for the short time period, the long retrieval time period button is deactivated.

17. The apparatus of claim 16 further comprising connection to an oxygen cannula.

18. The apparatus of claim 17 wherein said oxygen tube is connected to user tubing, and said user tubing is connected to the oxygen cannula.

19. The apparatus of claim 16 wherein said apparatus is connected to an oxygen source.

20. The apparatus of claim 16 further comprising a wireless communications device.

21. The apparatus of claim 16 further comprising a delay adjustment input device.

22. An apparatus for retrieval and storage of an oxygen tube comprising:
a motor attached to a rotatable spool, said rotatable spool enclosed in a housing;
a control system comprising a microprocessor, wherein said control system controls retrieving of the oxygen tube onto the rotatable spool or dispensing of the oxygen tube from the rotatable spool;
a tubing retainer disposed on a bottom of said apparatus, said tubing retainer securing a length of the oxygen tube;
retrieval buttons, said retrieval buttons comprising at least two buttons, one button to initiate a long retrieval time period over which a first length of the oxygen tube is retrieved onto the rotatable spool and one button to initiate a short retrieval time period over which a second length of oxygen tube is retrieved onto the rotatable spool;
a safety feature whereby upon initiation of the button for the long retrieval time period, the short retrieval time period button is deactivated, and whereby upon initiation of the button for the short time period, the long retrieval time period button is deactivated; and
an adjustable retrieval delay input device that delays activation of the retrieval time periods when any of the retrieval buttons are selected.

23. The apparatus of claim 22 further comprising connection to an oxygen cannula.

24. The apparatus of claim 23 wherein the first length of oxygen tube is connected to user tubing and the user tubing is connected to the oxygen cannula.

25. The apparatus of claim 22 wherein said apparatus is connected to an oxygen source.

26. The apparatus of claim 22 further comprising a wireless communications device.

* * * * *